(12) United States Patent
Tenne

(10) Patent No.: US 8,690,938 B2
(45) Date of Patent: Apr. 8, 2014

(54) OCCLUSION DEVICE COMBINATION OF STENT AND MESH WITH DIAMOND-SHAPED POROSITY

(75) Inventor: Dirk Tenne, Miami Beach, FL (US)

(73) Assignee: Depuy Synthes Products, LLC, Raynham, MA (US)

( * ) Notice: Subject to any disclaimer, the term of this patent is extended or adjusted under 35 U.S.C. 154(b) by 1515 days.

(21) Appl. No.: 11/420,519

(22) Filed: May 26, 2006

(65) Prior Publication Data

US 2007/0276469 A1   Nov. 29, 2007

(51) Int. Cl.
   *A61F 2/06* (2013.01)

(52) U.S. Cl.
   USPC .......................................................... 623/1.23

(58) Field of Classification Search
   USPC ........ 623/1.23, 1.17, 1.39, 1.4; 606/200, 191, 606/199
   See application file for complete search history.

(56) References Cited

U.S. PATENT DOCUMENTS

| | | | |
|---|---|---|---|
| 4,390,599 A | 6/1983 | Broyles | |
| 4,475,972 A * | 10/1984 | Wong | 156/167 |
| 4,864,824 A | 9/1989 | Gabriel et al. | |
| 4,981,756 A | 1/1991 | Rhandhawa | |
| 5,061,914 A | 10/1991 | Busch et al. | |
| 5,082,359 A | 1/1992 | Kirkpatrick | |
| 5,178,957 A | 1/1993 | Kolpe et al. | |
| 5,197,978 A | 3/1993 | Hess | |
| 5,288,230 A | 2/1994 | Nikutowski et al. | |
| 5,288,711 A | 2/1994 | Mitchell et al. | |
| 5,334,216 A | 8/1994 | Vidal et al. | |
| 5,360,397 A | 11/1994 | Pinchuk | |
| 5,403,700 A | 4/1995 | Heller et al. | |
| 5,516,781 A | 5/1996 | Morris et al. | |
| 5,543,019 A | 8/1996 | Lee et al. | |
| 5,563,146 A | 10/1996 | Morris et al. | |
| 5,607,463 A | 3/1997 | Schwartz et al. | |
| 5,629,077 A | 5/1997 | Turnlund et al. | |
| 5,646,160 A | 7/1997 | Morris et al. | |
| 5,656,036 A | 8/1997 | Palmaz | |
| 5,669,977 A | 9/1997 | Shufflebotham et al. | |
| 5,681,575 A | 10/1997 | Burrell et al. | |
| 5,683,453 A * | 11/1997 | Palmaz | 623/1.13 |

(Continued)

FOREIGN PATENT DOCUMENTS

| | | |
|---|---|---|
| EP | 0759730 | 5/1997 |
| EP | 0847733 A | 12/1997 |

(Continued)

OTHER PUBLICATIONS

Neurological Research, Lieber et al., The physics of endoluminal stenting in the treatment of cerebrovasilar aneurusms, 2002.

(Continued)

*Primary Examiner* — Gregory Anderson
*Assistant Examiner* — Christina Lauer
(74) *Attorney, Agent, or Firm* — Cook Alex Ltd.

(57) ABSTRACT

An occlusion device for implantation within a body vessel is provided with a screen member and an associated support member. The occlusion device is radially expandable from a compressed condition, suitable for inserting the device in an introducer, to a deployed or expanded condition within a vessel. The screen member includes a plurality of substantially diamond-shaped openings in the compressed and expanded conditions. The porosity of the screen member is less than the porosity of the support member in the expanded condition.

22 Claims, 4 Drawing Sheets

(56) References Cited

U.S. PATENT DOCUMENTS

| | | | |
|---|---|---|---|
| 5,685,961 | A | 11/1997 | Pourrezaei et al. |
| 5,735,892 | A | 4/1998 | Myers et al. |
| 5,744,958 | A | 4/1998 | Werne |
| 5,753,251 | A | 5/1998 | Burrell et al. |
| 5,766,710 | A | 6/1998 | Turnlund et al. |
| 5,770,255 | A | 6/1998 | Burrell et al. |
| 5,810,870 | A | 9/1998 | Myers et al. |
| 5,824,043 | A * | 10/1998 | Cottone, Jr. .................. 623/1.13 |
| 5,824,054 | A | 10/1998 | Khosravi et al. |
| 5,843,289 | A | 12/1998 | Lee et al. |
| 5,902,317 | A | 5/1999 | Kleshinski et al. |
| 5,908,409 | A | 6/1999 | Rinehart et al. |
| 5,925,038 | A | 7/1999 | Panescu et al. |
| 5,925,061 | A * | 7/1999 | Ogi et al. ........................ 623/1.2 |
| 5,925,075 | A | 7/1999 | Myers et al. |
| 5,938,697 | A | 8/1999 | Killion et al. |
| 5,945,153 | A | 8/1999 | Dearnaley |
| 5,951,586 | A | 9/1999 | Berg et al. |
| 6,015,402 | A | 1/2000 | Sahota |
| 6,017,553 | A | 1/2000 | Burrell et al. |
| 6,027,526 | A | 2/2000 | Limon et al. |
| 6,043,451 | A | 3/2000 | Julien et al. |
| 6,071,305 | A * | 6/2000 | Brown et al. ................ 623/1.43 |
| 6,096,175 | A | 8/2000 | Roth |
| 6,174,329 | B1 | 1/2001 | Callol et al. |
| 6,203,732 | B1 | 3/2001 | Clubb et al. |
| 6,238,686 | B1 | 5/2001 | Burrell et al. |
| 6,270,872 | B1 | 8/2001 | Cline et al. |
| 6,296,661 | B1 * | 10/2001 | Davila et al. ................. 623/1.13 |
| 6,312,463 | B1 | 11/2001 | Rourke et al. |
| 6,319,277 | B1 | 11/2001 | Rudnick et al. |
| 6,322,588 | B1 | 11/2001 | Ogle et al. |
| 6,325,824 | B2 | 12/2001 | Limon |
| 6,342,067 | B1 | 1/2002 | Mathis et al. |
| 6,432,116 | B1 | 8/2002 | Callister et al. |
| 6,436,132 | B1 | 8/2002 | Patel et al. |
| 6,447,478 | B1 | 9/2002 | Maynard |
| 6,471,721 | B1 | 10/2002 | Dang |
| 6,527,919 | B1 | 3/2003 | Roth |
| 6,533,905 | B2 | 3/2003 | Johnson et al. |
| 6,537,310 | B1 | 3/2003 | Palmaz et al. |
| 6,605,111 | B2 | 8/2003 | Bose et al. |
| 6,627,246 | B2 | 9/2003 | Mehta et al. |
| 6,645,243 | B2 | 11/2003 | Vallana et al. |
| 6,660,032 | B2 | 12/2003 | Klumb et al. |
| 6,666,882 | B1 | 12/2003 | Bose et al. |
| 6,673,106 | B2 | 1/2004 | Mitelberg et al. |
| 6,726,993 | B2 | 4/2004 | Teer et al. |
| 6,786,920 | B2 | 9/2004 | Shannon et al. |
| 6,805,898 | B1 | 10/2004 | Wu et al. |
| 6,818,013 | B2 | 11/2004 | Mitelberg et al. |
| 6,865,810 | B2 | 3/2005 | Stinson |
| 6,938,668 | B2 | 9/2005 | Whicher et al. |
| 6,955,685 | B2 | 10/2005 | Escamilla et al. |
| 2001/0037808 | A1 * | 11/2001 | Deem et al. .............. 128/200.24 |
| 2001/0039449 | A1 | 11/2001 | Johnson et al. |
| 2004/0098094 | A1 * | 5/2004 | Boyle et al. .................. 623/1.13 |
| 2005/0010175 | A1 | 1/2005 | Beedon et al. |
| 2005/0154449 | A1 | 7/2005 | Elmaleh |
| 2008/0004653 | A1 * | 1/2008 | Sherman et al. .............. 606/195 |
| 2008/0097495 | A1 * | 4/2008 | Feller, III et al. ............. 606/157 |

FOREIGN PATENT DOCUMENTS

| | | |
|---|---|---|
| EP | 0641224 B1 | 8/1998 |
| EP | 1099004 A1 | 7/1999 |
| EP | 0824900 B1 | 4/2003 |
| EP | 01099004 B1 | 9/2004 |
| GB | 2331998 A | 6/1999 |
| WO | 9307924 A1 | 4/1993 |
| WO | 9323092 A1 | 11/1993 |
| WO | 9425637 A1 | 11/1994 |
| WO | 9513704 A1 | 5/1995 |
| WO | 9726026 A2 | 7/1997 |
| WO | 9966966 A1 | 12/1999 |
| WO | 0004204 A1 | 1/2000 |

OTHER PUBLICATIONS

American Journal of Neuroradiology, Higashida et al., Initial clinical experience with a new self-expanding nitinol stent for the treatment of intracranial cerebral aneurysms: the Cordis Enterprise stent, Aug. 2005.

Spine; Hellier, Hedman, Kostuik; Wear Studies for development of an intervertebral disc prosteses; Jun. 1992; US.

Biomateriais; Li; Behaviour of titanium and titania-based ceramics in vitro and in vivo; Feb. 2003; US.

Elsevier; Banks et al.; Ion bombardment modification of surfaces in biomedical applications; 399-434; 1984; Netherlands.

Advances in Bioengineering; Chung, Chang, Han; Development of thin metal film deposition process for the intravascular catheter; Conference; Nov. 14, 1999; US.

Journal of Materials Processing Technology; Kola, Daniels, Cameron, Hashmi; Magnetron suputtering of TiN protective coatings for medical applications; 422-430; Jan. 1996; Ireland.

Journal of Biomedical Materials Research; Yuhta et al.; Blood compatibility of sputter deposited alumina films; 271-224; Feb. 1994.

Society for Biomateriais; Ong, Lucas, Lacefield, Rigney; Properties of calcium-phosphate coatings produced by ion-beam sputter deposition; Conference; May 1, 1991; US.

Asaio; Zabetakis, Cotell, Chrisey, Auyeung; Pulsed laser deposition of thin film hydroxyapatite. Applications for flexible catheters; 896-899; Jul. 1994; US.

* cited by examiner

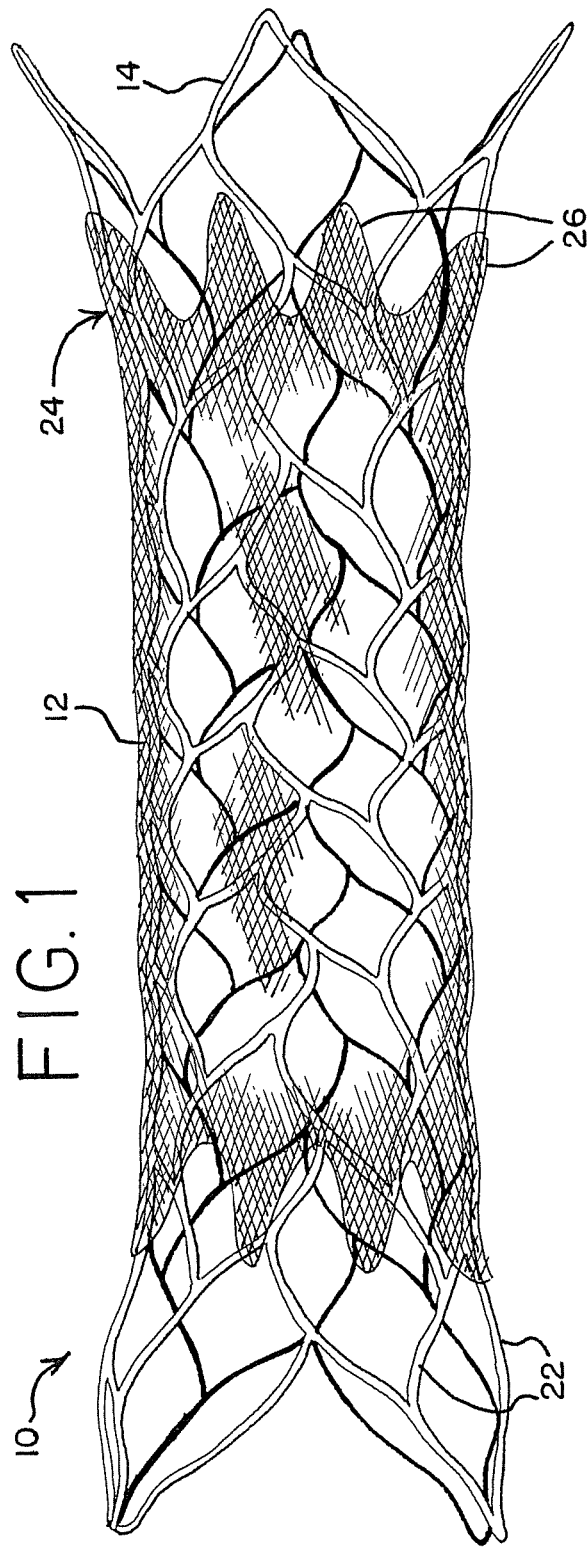
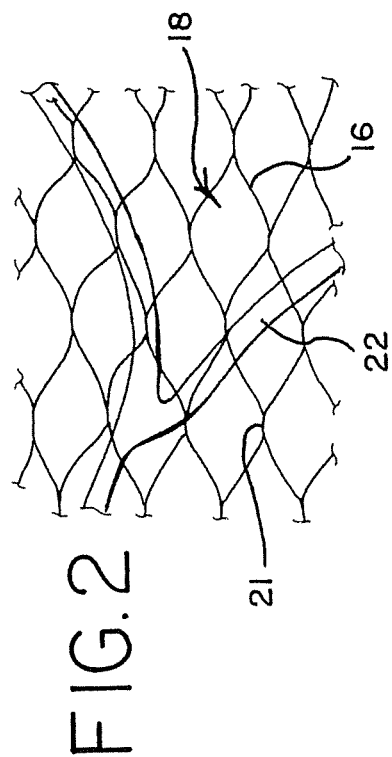

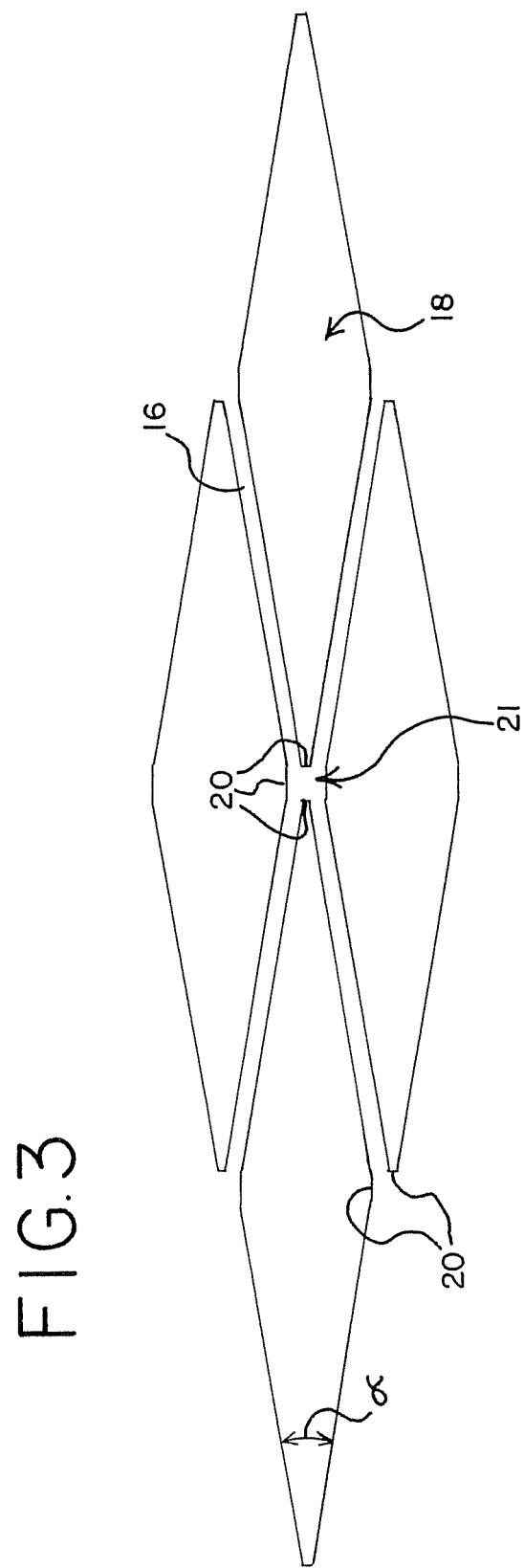

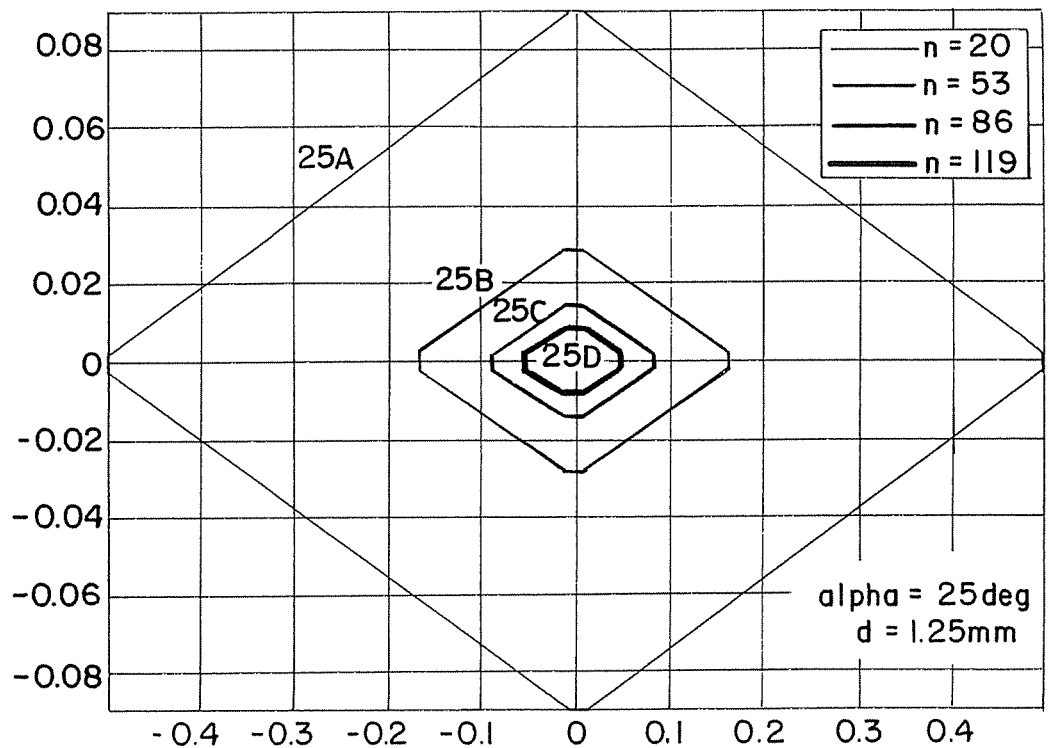
FIG. 4  DIAMOND CELLS WITH CONSTANT OPENING ANGLE AND CHANGING POROSITY
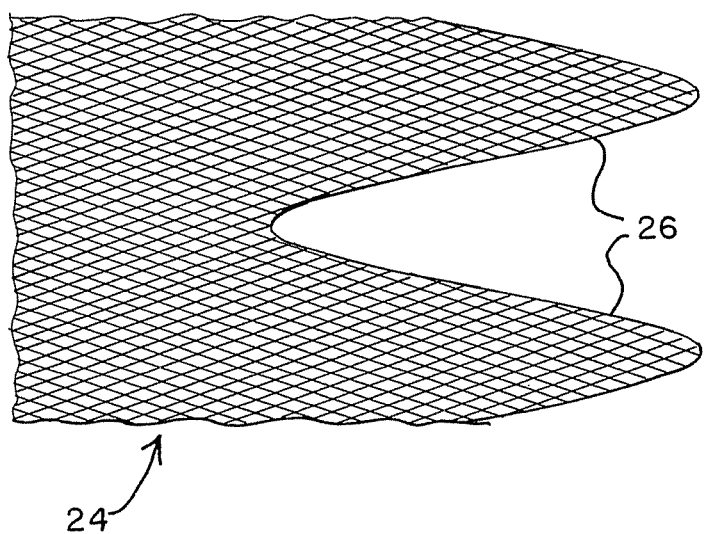
FIG. 5

OCCLUSION DEVICE COMBINATION OF STENT AND MESH WITH DIAMOND-SHAPED POROSITY

FIELD OF THE INVENTION

This invention generally relates to medical devices that are implantable within a human subject and that have occlusion capabilities for treating defective or diseased body vessels. More particularly, this invention relates to an occlusion device including a support member and a screen member.

DESCRIPTION OF RELATED ART

Medical devices that can benefit from the present invention include those that are characterized by hollow interiors and that are introduced endoluminally and expand when deployed so as to protect or plug up a location of concern within the patient. These are devices that move or are moved between collapsed and expanded conditions or configurations for ease of deployment through catheters and introducers. The present disclosure focuses upon occlusion devices for diseased locations within vessels of the body, especially devices sized and configured for implantation within the vasculature, as well as devices for neurovascular use.

Endoluminal stents typically have a relatively open structure, with pores or openings in the surface that can allow for endothelialization and more permanent fixture of the stent within the vessel after implantation. Certain stents have an especially open structure in order to allow blood flow through the openings and to peripheral arteries after implantation of the stent adjacent to an aneurysm. Typically, the pores or openings are added by masking and/or etching techniques or laser or water jet cutting.

When thin film meshes are combined with a stent, the mesh typically is provided with a porosity less than that of a stent when expanded or deployed within a body vessel. Thus, they are useful for applications requiring a lower porosity. However, meshes are generally not rugged enough for a wide range of applications, such as supporting a stenosed vessel, and they typically can be provided with a skeletal support structure, oftentimes a stent. Examples of implantable grafts used in combination with an underlying support structure can be seen in Boyle, Marton and Banas U.S. Patent Application Publication No. 2004/0098094, which is hereby incorporated by reference hereinto. This publication proposes implantable endoluminal grafts having a pattern of slit openings that move from a closed condition to an open condition that could be characterized as having a generally diamond-shaped condition. Underlying structural support elements support the microporous metallic thin film graft. One potential drawback of the grafts is that the transition from the closed slit shape to the open diamond shape can be overly stressful on the film, especially at the ends of the slit, thereby leading to film rupture during deployment.

Accordingly, a general aspect or object of the present invention is to provide an occlusion device less susceptible to film rupture during deployment.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with an aspect of the present invention, an occlusion device includes a generally tubular support member radially expandable from a compressed condition to an expanded condition for occlusion action within a body vessel. The occlusion device also includes a generally tubular screen member associated with at least a portion of the support member and radially expandable from a compressed condition to an expanded condition with the support member. The screen member further includes a plurality of openings that are substantially diamond-shaped in the compressed condition and in the expanded condition. The support member and screen member each have a porosity in the expanded condition, with the porosity of the screen member being less than that of the support member.

In accordance with another aspect of the present invention, an occlusion device includes a generally tubular inner support member radially expandable from a compressed condition to an expanded condition for occlusion action within a body vessel. A generally tubular outer support member and a generally tubular screen member are also radially expandable with the inner support member. The screen member is received between at least a portion of the inner support member and at least a portion of the outer support member. The screen member includes a plurality of openings that are substantially diamond-shaped in the compressed condition and in the expanded condition. The support members and screen member each have a porosity in the expanded condition, with the porosity of the screen member being less than that of the support members.

In accordance with yet another aspect of the present invention, an occlusion device includes a generally tubular support member radially expandable from a compressed condition to an expanded condition for occlusion action within a body vessel. A generally tubular inner screen member, which is at least partially received within the support member, and a generally tubular outer screen member, which overlays at least a portion of the support member, are also radially expandable with the support member. The screen members include a plurality of openings that are substantially diamond-shaped in the compressed condition and in the expanded condition. The support member and screen members each have a porosity in the expanded condition, with the porosities of the screen members being less than that of the support member.

BRIEF DESCRIPTION OF THE DRAWINGS

FIG. 1 is a side elevational view of an occlusion device according to an aspect of the present invention, with some parts broken away for clarity;

FIG. 2 is a detail view of a portion of the occlusion device of FIG. 1;

FIG. 3 is an enlarged plan view of a diamond cell pattern suitable for application to a screen member;

FIG. 4 is a graphical view of an array of various diamond cells at a given opening angle;

FIG. 5 is a detail view of a screen member edge with a generally sinusoidal configuration;

DESCRIPTION OF THE PREFERRED EMBODIMENTS

Figure 6:
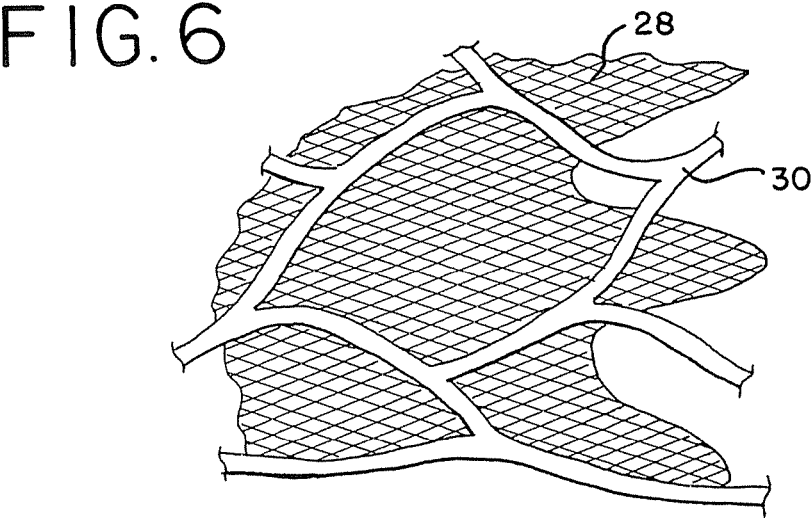
FIG. 6 is a detail view of an occlusion device according to another aspect of the present invention.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The occlusion device 10 of FIG. 1 is a generally tubular structure with a generally tubular screen member 12 and a generally tubular support member 14. The screen member 12 is illustrated in FIG. 1 with selected portions broken away to show an underlying portion of the support member 14. The occlusion device 10 and its constituent parts are radially expandable from a compressed condition, for delivery in an introducer, to an expanded condition within a body vessel to support the same. An occlusion device according to the present invention may be deployed with known devices and according to known methods.

In the illustrated embodiment of FIG. 1 and FIG. 2, the screen member 12 overlays at least a portion of the support member 14. Preferably, the screen member 12 is provided as a mesh which is comprised of a plurality of cells 16 defining substantially diamond-shaped openings 18. These cells 16 are referred to herein as "diamond cells" and can be seen in greater detail in FIG. 3 as unexpanded and in FIG. 2 as expanded. As will be appreciated from the description herein, the risk of film rupture is substantially decreased because the openings 18 are initially formed with a diamond shape, so as to address the prior art problems associated with transitioning substantially linear closed slits to open during deployment. The present diamond-shaped openings in the manufactured condition avoid or minimize stress and fissures that tend to develop during expansion.

According to one method of manufacturing the screen member 12, a substantially cylindrical mandrel (not illustrated) is provided. In one embodiment, the mandrel has a diameter of 1.25 mm and is formed of copper. A thin film is formed on the mandrel according to known methods, such as sputtering, and diamond-shaped openings are formed in the film, preferably by laser cutting. Forming the openings as diamonds on a mandrel reduces the material ratio and increases the capability of loading the occlusion device into an introducer.

FIG. 3 illustrates a pattern that may be repeated along the thin film to create the diamond cells 16. As illustrated in FIGS. 3 and 4, the diamond-shaped openings 18 may be provided with flattened or blunted corners 20 without departing from the scope of the present invention. At smaller opening sizes, it can become difficult to accurately manufacture tight, angular corners and, even if possible, it may be preferred to flatten or round the corners in order to provide more material between adjacent openings, and thereby further discourage film rupture. For example, as best illustrated in FIG. 3, four corners of adjacent openings 18 define a junction or bridge 21. The heightened amount of material at the bridges 21 (compared to the width of the material between the edges of adjacent openings 18) prevents the corners 20 from rupturing. The amount of material may be increased by flattening or rounding some or all of the corners meeting at the bridge 21. In a preferred embodiment, which succeeds in balancing the competing interests of rupture prevention and maintenance of a high opening-to-material ratio, the lateral corners of each opening 18 are flattened or rounded, while the upper and lower corners are relatively sharp.

Hence, when used herein to describe the shape of the openings as-manufactured or in a compressed or expanded condition, the term "diamond-shaped" includes diamonds with one or more flattened or blunted or rounded corners and/or diamonds with edges having some degree of curvature.

Preferably, the screen member is provided with identical diamond cells arranged in a uniform pattern, which results in substantially uniform radial expansion properties at all points of the screen member. Alternatively, the diamond-shaped openings may be provided in a non-uniform array or differently sized diamond openings may be formed along the surface of the thin film.

The diamond openings 18 of FIG. 3 are illustrated with an identical as-manufactured opening angle "$\alpha$", such as between about 10 and 40 degrees, typically between about 20 and 35 degrees, and may be approximately 25 degrees in one angle embodiment. As shown in FIG. 4, a range of opening sizes 25A, 25B, 25C, 25D are possible for a given opening angle "$\alpha$". In general, the size of the openings is directly related to the porosity of the screen member, such that larger openings will result in greater porosity. Porosity can be varied without changing the opening angle. The number of openings about a circumference of the screen member, that number designated in FIG. 4 as "n", depends on several factors, including the size of the openings. For example, it has been found that approximately 119 smaller openings 25D or 20 larger openings 25A can be placed about a circumference of a screen member formed on a mandrel having a diameter "d" of 1.25 mm, as illustrated graphically in FIG. 4. It will be appreciated that more or fewer openings may be provided without departing from the scope of the present invention. Other factors that determine the number of openings include the diameter of the screen member and the spacing between the openings.

Preferably, the openings are sufficiently spaced to result in an opening-to-material ratio falling within the range of approximately 1.5:1 (or approximately 60% open space and 40% film material) and 4:1 (or approximately 80% open space and 20% film material). In one embodiment, a thin film is applied to a mandrel diameter of 1.5 mm, and then the pattern of FIG. 3 is repeated 40 times around a circumference of the film, with an opening angle of 25 degrees and spacing between adjacent openings of 0.007 mm, also referred to as the strut width. Typical strut widths can be between about 0.005 and 0.01 mm.

The screen member 12 is radially expandable from a compressed or delivery condition to an expanded or deployed condition, so it is preferably formed of a deformable or semi-rigid material, may have shape memory attributes or not, and may be polymeric or metallic. Suitable polymeric materials include polyolefins such as polypropylenes, polyesters such as polyethylene terephthalate, polyamides, nylons and so forth. Typical screen members will have a thickness of between about 0.05 and about 0.1 mm, such as between about 0.07 and 0.08 mm.

If provided as a metal, the screen member 12 may be substantially comprised of, for example, stainless steel or an alloy such as nickel and titanium alloys or nitinols. Nitinol type metals typically will exhibit superelastic properties. Shape memory materials such as nitinols in an austenite state can be used.

More particularly, when the material is a nitinol, the nitinol may be either a martensite or austenite thin film at human body temperature, which will result in different performance characteristics. If the nitinol is a martensite thin film at body temperature, then it will easily be compressed and inserted into a delivery catheter, then allow radial expansion of the occlusion device without resistance. A martensitic or superelastic nitinol is more likely to easily "go along for the ride" with the support member 14, especially when it expands. If a shape-memory material such as a nitinol is an austenite thin film at body temperature, then the screen member will actively return to its as formed shape if the occlusion device is being designed to facilitate its recapture after being deployed in a body vessel.

The support member 14 preferably is provided as a radially expandable, generally tubular stent, as illustrated in FIG. 1. The support member 14 may take on many different patterns or configurations, such as a self-expanding stent, such as those disclosed in U.S. Pat. Nos. 6,673,106 and 6,818,013, both to Mitelberg et al. and both of which are hereby incorporated herein by reference. Alternatively, the support member may be provided as a balloon-expandable stent.

The illustrated support member 14 of FIG. 1 is a self-expanding stent, preferably laser cut from a tubular piece of nitinol to form a skeletal structure. The skeletal structure has a thin wall, a small diameter, and when cut forms a plurality of cells which are created by a plurality of interconnected struts 22. The nitinol is preferably treated so as to exhibit superelastic properties at body temperature.

According to one aspect of the present invention, illustrated in FIGS. 1 and 2, the occlusion device is comprised of a screen member 12 overlaying at least a portion of a support member 14. The screen member 12 may be fully or partially affixed to the support member 14 in order to prevent the two from rotating or otherwise moving with respect to each other. Suitable joinder means will depend on the nature of the screen member 12 and on the support member 14, the selection of which means is a routine task for one of ordinary skill in the art. This means may include, but is not limited to, welding, soldering, adhering, crimping, or combinations thereof.

In use, the occlusion device 10 is radially compressed into a delivery condition and inserted into the distal end of an introducer (not shown). The occlusion device 10 may be mounted about a guidewire or a balloon catheter before being compressed and inserted into the introducer. When the occlusion device 10 is compressed, the openings 18 of the screen member 12 move from the relatively open diamond shape of FIGS. 1 and 2 to a more closed diamond shape having a smaller opening angle "a" in the compressed condition.

In order to simplify insertion of the occlusion device 10 into the introducer, the peripheral edges at the axial ends of the screen can be non-linear, in that they do not lie fully within a radial plane. They do not follow a circular path but instead follow an undulating path to provide "wavy ends." For example, the proximal edge 24 of the screen member 12 may be provided with a generally sinusoidal configuration, as illustrated in greater detail in FIG. 5. A flat or non-undulating edge may become folded upon itself when compressed and inserted into an introducer, thereby increasing friction and the associated push forces. This is analogous to folding that occurs when a mitten is forced into a tight pocket. In the embodiment of FIGS. 1 and 5, extensions 26 of the edge 24 may move toward each other without overlapping when the device is compressed, analogous to gloved fingers moving together when inserted into a tight pocket.

When the occlusion device 10 has been properly loaded, the introducer is moved into the interior of a body vessel and positioned adjacent to a region of the vessel which is to be occluded. Finally, the occlusion device 10 is ejected from the introducer and into the target region. If the support member is not self-expanding, then a balloon is expanded to force the occlusion device 10 against the wall of the vessel.

The screen member 12 and the support member 14 each have a separate porosity in the deployed or expanded condition of FIG. 1. As illustrated, the porosity of the screen member 12 is less than that of the support member 14, which effectively gives the occlusion device 10 an overall porosity less than that of the support member 14 alone.

The occlusion device may be provided according to a number of various configurations in order to achieve results similar to those described above with regard to the embodiment of FIG. 1. For example, according to one aspect of the present invention, a generally tubular screen member 28 instead may be mounted within a generally tubular support member 30, as illustrated in FIG. 6. With this approach, the support member is external of the screen member.

Figure 7:
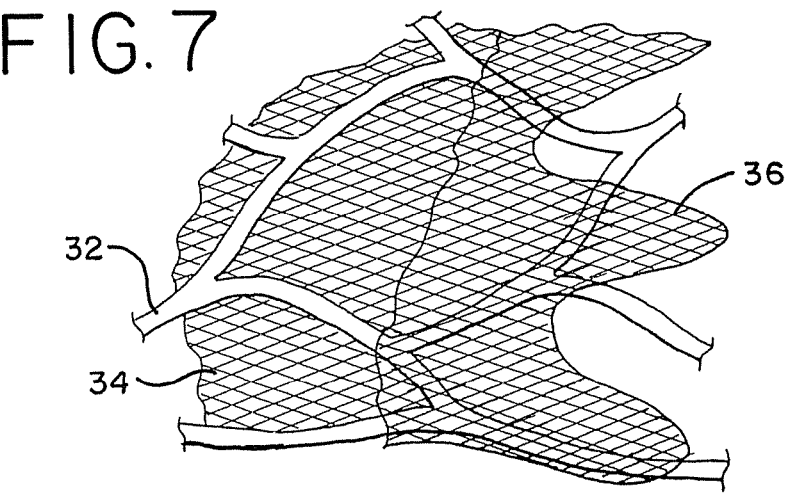
FIG. 7 is a detail view of an occlusion device according to yet another aspect of the present invention, with some parts broken away for clarity.

According to yet another aspect, illustrated in FIG. 7, an occlusion device may be provided with a generally tubular support member 32, a generally tubular inner screen member 34 at least partially received within the support member 32, and a generally tubular outer screen member 36 overlaying at least a portion of the support member 32. Each screen member can be secured to the support member. Also, rather than individually attaching each screen member 34 and 36 to the support member 32, the screen members 34 and 36 may be directly attached to each other, thereby trapping the support member 32.

Figure 8:
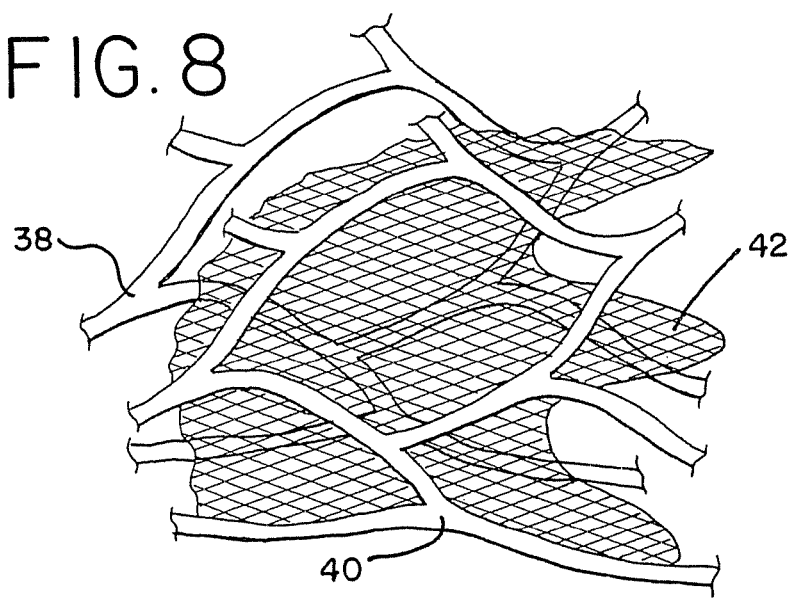
FIG. 8 is a detail view of an occlusion device according to still another aspect of the present invention.

According to still another aspect, illustrated in FIG. 8, an occlusion device may be provided with a generally tubular inner support member 38, a generally tubular outer support member 40, and a generally tubular screen member 42 received between at least a portion of the inner support member 38 and at least a portion of the outer support member 40. Each support member can be secured to the sandwiched screen member. Also, rather than individually attaching each support member 38 and 40 to the screen member 42, the support members 38 and 40 may be directly attached to each other, thereby trapping the screen member 42.

It is to be understood that the various screen members and support members of FIGS. 6-8 conform to the above description of the components of the occlusion device 10 of FIG. 1. Hence, each screen member is radially expandable with the associated support member, has a plurality of substantially diamond-shaped openings in both the compressed and expanded conditions, and has a porosity that is less than that of the associated support member in the expanded condition within a body vessel.

The screen member and/or the support member may be coated with an agent, such as heparin or rapamycin, to prevent stenosis or restenosis of the vessel. Examples of such coatings are disclosed in U.S. Pat. Nos. 5,288,711 to Mitchell et al.; 5,516,781 to Morris et al.; 5,563,146 to Morris et al.; and 5,646,160 to Morris et al., all of which are hereby incorporated herein by reference. Other coatings may also be applied without departing from the scope of the present invention.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An occlusion device for occluding at least a portion of a body vessel in a human subject, comprising:
   a generally tubular stent radially and circumferentially expandable from a compressed condition to an expanded condition for occlusion action within a body vessel, wherein the stent has a porosity in at least the expanded condition;
   a generally tubular screen member associated with at least a portion of the stent, said screen member having a compressed, unexpanded condition and an expanded condition, said screen member being radially and circumferentially expandable with the stent from said compressed, unexpanded condition to said expanded condition, further comprising a plurality of substantially diamond-shaped cut-out openings that are diamond-shaped in both the compressed, unexpanded condition and in the expanded condition, wherein the screen member is a thin-film mesh from which the diamond-shaped openings had been cut and that has a porosity in the expanded condition less than the porosity of the stent in the expanded condition;

the mesh of the screen member at the compressed, unexpanded condition has a plurality of bridges at corners of the cut-out diamond-shaped openings, each bridge having four cut-out blunted corners, each blunted corner joining and spacing apart two adjacent struts that flank the blunted corner, each blunted corner has an amount of material of the mesh between its two spaced-apart struts at the location that each strut joins the bridge, the amount of blunted corner material at each of the four corners being wider than the combined width of the two adjacent struts joined to the bridge at each said blunted corner, the width of each strut of the mesh being between about 0.005 and 0.01 mm;

two of said four cut-out blunted corners are opposite each other and are lateral corners that join two adjacent spaced-apart struts, and each cut-out lateral corner is flattened or rounded in the compressed, unexpanded condition; and the other two of said four cut-out blunted corners are opposite each other and are upper and lower corners respectively that join two adjacent spaced-apart struts positioned with respect to each other at an opening angle in their compressed, unexpanded condition of between about 20 and 35 degrees whereby the opening angle of each cut-out upper and lower corner is sharper than that of either cut-out lateral corner.

2. The occlusion device of claim 1, wherein the screen member overlays at least a portion of the stent.

3. The occlusion device of claim 2, further including an additional screen member having a plurality of diamond-shaped openings, and wherein the stent overlays said additional screen member.

4. The occlusion device of claim 1, wherein at least a portion of the screen member is received within the stent.

5. The occlusion device of claim 4, further including an additional stent, and wherein the screen member overlays at least a portion of said additional stent.

6. The occlusion device of claim 1, wherein an edge of the screen member has a generally sinusoidal configuration.

7. The occlusion device of claim 1, wherein said screen member has an opening-to-material ratio falling within the range of approximately 1.5:1 and approximately 4:1.

8. The occlusion device of claim 1, wherein said screen member is substantially comprised of a material having shape memory properties.

9. The occlusion device of claim 8, wherein said material having shape memory properties is nitinol.

10. The occlusion device of claim 9, wherein said nitinol is a martensite thin film at human body temperature.

11. The occlusion device of claim 9, wherein said nitinol is an austenite thin film at human body temperature.

12. The occlusion device of claim 1, wherein said screen member is substantially comprised of a polymeric material.

13. An occlusion device for occluding at least a portion of a body vessel in a human subject, comprising:

A generally tubular stent radially and circumferentially expandable from a compressed condition to an expanded condition for occlusion action within a body vessel, wherein the stent has a porosity in at least the expanded condition;

a generally tubular screen member extending with and received on at least a portion of the stent, said screen member having a compressed, unexpanded condition and an expanded condition, said screen member being radially and circumferentially expandable with the stent from said compressed, unexpanded condition to said expanded condition, the screen member further comprising a plurality of substantially diamond-shaped cut-out openings in both the compressed, unexpanded condition and in the expanded condition, wherein the screen member is a thin-film mesh from which the diamond-shaped openings had been cut and that has a porosity in the expanded condition less than the porosity of the stent in the expanded condition;

the mesh of the screen member at the compressed, unexpanded condition has a plurality of bridges at corners of the cut-out diamond-shaped openings, each bridge having four cut-out blunted corners, each blunted corner joining and spacing apart two struts that flank the blunted corner, each blunted corner has an amount of material of the mesh between its two spaced-apart struts at the that each strut joins the bridge, the amount of blunted corner material at each of the four corners being wider than the combined width of the two adjacent struts joined to the bridge at each said blunted corner, the width of each strut of the mesh being between about 0.005 and 0.01 mm;

two of said four cut-out blunted corners are opposite each other and are lateral corners that join two adjacent spaced-apart struts, and each cut-out lateral corner is flattened or rounded in the compressed, unexpanded condition;

the other two of said four cut-out blunted corners are opposite each other and are upper and lower corners respectively that join two adjacent spaced-apart struts positioned with respect to each other at an opening angle in their compressed, unexpanded condition of between about 20 and 35 degrees whereby the opening angle of each cut-out upper and lower corner is sharper than that of either cut-out lateral corner; and said screen member is comprised of a nitinol material and has an opening-to-material ratio falling within the range of approximately 1.5:1 and approximately 4:1.

14. The occlusion device of claim 13, wherein an edge of the screen member has a generally sinusoidal configuration.

15. The occlusion device of claim 13, wherein said screen member diamond-shaped openings impart a porosity to said screen member of between about 60 percent and 80 percent.

16. The occlusion device of claim 13, wherein said nitinol is a martensite thin film at human body temperature.

17. The occlusion device of claim 13, wherein said nitinol is an austenite thin film at human body temperature.

18. An occlusion device for occluding at least a portion of a body vessel in a human subject, comprising:

a generally tubular stent radially expandable from a compressed condition to an expanded condition for occlusion action within a body vessel, wherein the stent has a porosity in at least the expanded condition;

a generally tubular inner screen member at least partially received within the stent, said screen member having a compressed, unexpanded condition and an expanded condition, said screen member being radially and circumferentially expandable with the stent from said compressed, unexpanded condition to said expanded condition, the screen member being a thin-film mesh from which diamond-shaped openings had been cut and having a plurality of the cut-out substantially diamond-shaped openings in both the compressed, unexpanded condition and in the expanded condition;

a generally tubular outer screen member overlaying at least a portion of the stent and radially and circumferentially expandable from a compressed, unexpanded condition to an expanded condition with the stent, the screen member being a thin-film mesh from which diamond-shaped openings had been cut and having a plurality of the cut-out substantially diamond-shaped openings in both the compressed, unexpanded condition and in the expanded condition, wherein at least one of the screen members has a porosity in the expanded condition less than the porosity of the stent in the expanded condition;

the mesh of each of the inner and outer screen members at the compressed, unexpanded condition has a plurality of bridges at corners of the cut-out diamond-shaped openings, each bridge having four cut-out blunted corners, each blunted corner joining and spacing apart two adjacent struts that flank the blunted corner, each blunted corner has an amount of material of the mesh between its two spaced-apart struts at the location that each strut joins the bridge, the amount of blunted corner material at each of the four corners being wider than the combined width of the two adjacent struts joined to the bridge at each said blunted corner, the width of each strut of the mesh being between about 0.005 and 0.01 mm;

two of said four cut-out blunted corners are opposite each other and are lateral corners that join two adjacent spaced-apart struts, and each cut-out lateral corner is flattened or rounded in the compressed, unexpanded condition; and the other two of said four cut-out blunted corners are opposite each other and are upper and lower corners respectively that join two adjacent spaced-apart struts positioned with respect to each other at an opening angle in their compressed, unexpanded condition of between about 20 and 35 degrees whereby the opening angle of each cut-out upper and lower corner is sharper than that of either cut-out lateral corner.

19. The occlusion device of claim 18, wherein each screen member has an edge of a generally sinusoidal configuration.

20. The occlusion device of claim 18, wherein each said screen member has an opening-to-material ratio falling within the range of approximately 1.5:1 and approximately 4:1.

21. The occlusion device of claim 18, wherein said screen members are substantially comprised of a material having superelastic properties.

22. The occlusion device of claim 21, wherein said material having superelastic properties is nitinol.

* * * * *